United States Patent [19]

Cody et al.

[11] Patent Number: 5,260,276
[45] Date of Patent: Nov. 9, 1993

[54] LINEAR AND MONOCYCLIC ENDOTHELIN ANTAGONISTS

[75] Inventors: Wayne L. Cody, Saline; Annette M. Doherty; John X. He, both of Ann Arbor, all of Mich.

[73] Assignee: Warner-Lambert Company, Morris Plains, N.J.

[21] Appl. No.: 715,934

[22] Filed: Jun. 14, 1991

[51] Int. Cl.$^5$ .................. A61K 37/02; C07K 7/06; C07K 7/08
[52] U.S. Cl. ........................... 514/14; 514/13; 514/15; 514/16; 514/17; 514/18; 530/326; 530/327; 530/328; 530/329; 530/330; 530/331; 530/317
[58] Field of Search ............... 514/13, 14, 15, 16, 514/17, 18; 530/326, 327, 328, 329, 330, 331, 317

[56] References Cited

U.S. PATENT DOCUMENTS 4,981,950  1/1991  Masaki et al. ................ 530/326
5,114,918  5/1992  Ishikawa et al. .............. 514/11

OTHER PUBLICATIONS

Cody, W. et al., Chem. Abs., CA 116(11):99469h, 1992.
Komagaye, S. et al., *Int. J. Peptide Prot. Res.*, 32:519–526, 1988.
Stewart, J. et al., *Solid Phase Peptide Synthesis* Pierce Chemical. Co., 1984.
Cody, W. L., et al. Abstract, Second International Conference on Endothelin, Tsukuba, Japan, Dec. 9, 1990.
Johansen, N. L., et al. Peptides 1990, Proceedings of the Twenty-First European Peptide Symposium, edited by Giralt, E. & Andreu, D., pp. 680–681, ESCOM Science Publishers B.V. (1990).

*Primary Examiner*—Lester L. Lee
*Attorney, Agent, or Firm*—Francis J. Tinney

[57] ABSTRACT

Novel linear and monocyclic antagonists of endothelin are described, as well as methods for the preparation and pharmaceutical compositions of the same, which are useful in controlling hypertension, myocardial infarction, metabolic, endocrinological, and neurological disorders, congestive heart failure, endotoxic shock, subarachnoid hemorrhage, arrhythmias, asthma, acute renal failure, preeclampsia, and diabetes.

7 Claims, No Drawings

LINEAR AND MONOCYCLIC ENDOTHELIN ANTAGONISTS

BACKGROUND OF THE INVENTION

The present invention relates to novel linear and monocyclic antagonists of endothelin useful as pharmaceutical agents, to methods for their production, to pharmaceutical compositions which include these compounds and a pharmaceutically acceptable carrier, and to pharmaceutical methods of treatment. More particularly, the novel compounds of the present invention are antagonists of endothelin useful in controlling hypertension, myocardial infarction, metabolic, endocrinological, and neurological disorders, congestive heart failure, endotoxic shock, subarachnoid hemorrhage, arrhythmias, asthma, acute renal failure, preeclampsia, and diabetes.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs). The unique bicyclic structure and corresponding arrangement of the disulfide bridges of ET-1, which are the same for the endothelins, VIC, and the sarafotoxins, has led to significant speculation as to the importance of the resulting induced secondary structure to receptor binding and functional activity. ET-1 analogues with incorrect disulfide pairings exhibit at least 100-fold less vasoconstrictor activity. The flexible C-terminal hexapeptide of ET-1 has been shown to be important for binding to the ET receptor and functional activity in selected tissues. Additionally, the C-terminal amino acid (Trp-21) has a critical role in binding and vasoconstrictor activity, since ET[1-20] exhibits approximately 1000-fold less functional activity.

Cody, W. L., et al, Abstract, Second International Conference on Endothelin, Tsukuba, Japan, Dec. 9, 1990, and Johansen, N. L., et al, Peptides 1990, Proceedings of the Twenty First European Peptide Symposium, edited by Giralt, E. and Andreu, D., pages 680–681, Escom Science Publishers B.V. (1990) disclosed various monocyclic analogs of ET-1, none of which exhibited any functional vasoconstricting activity.

However, we have surprisingly and unexpectedly found that a series of linear and monocyclic analogs of ET-1 are antagonists of endothelin.

SUMMARY OF THE INVENTION

Accordingly, the present invention is a compound of Formula I $$AA^1{-}R{-}R^1{-}R^2{-}AA^{1a}{-}AA^2{-}AA^4{-}AA^3{-}AA^5 \text{ Seq ID No: 1}$$

wherein
$AA^1$ is

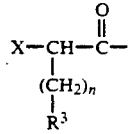

wherein
X is
  hydrogen,
  alkyl,
  alkenyl,
  alkynyl,
  cycloalkyl,
  heterocycloalkyl,
  aryl, or
  heteroaryl,
n is zero or an integer of 1, 2, 3, 4, 5, or 6,
$R^3$ is $-S-R^4$, wherein $R^4$ is as defined hereinafter,

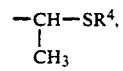

wherein $R^4$ is as defined hereinafter,
$-C(CH_3)_2-S-R^4$, wherein $R^4$ is
  hydrogen,
  alkyl, cycloalkyl, aryl, heteroaryl, or $R^4$ is absent when $AA^1$ is covalently linked to $AA^{1a}$ through a disulfide bridge,

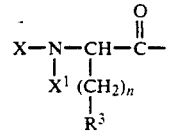

wherein X and $X^1$ are each the same or different and each is as defined above for X or $X^1$ is Asp-Lys Glu and n and $R^3$ are as defined above,

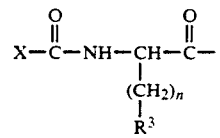

wherein X, n, and $R^3$ are as defined above, or

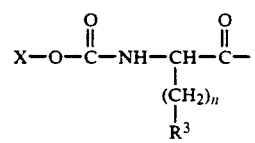

wherein X, n, and $R^3$ are as defined above;
R is absent or is one to four amino acids selected from the group consisting of:
  Ala,
  Arg,
  Asn,
  Asp,
  Cys,
  Glu,
  Gln,
  Gly, His,
Ile,
Leu,
Lys,
Met,
Phe,
Pro,
Ser,
Thr,
Trp,
Tyr,
Val,
3Hyp,
4Hyp,
Hcy,
Nva,
Nle,
Orn,
Abu,
Ahe,
Acp,
Aoc,
Apn,
Chx,
Cit,
HomoPhe,
1-Nal,
2-Nal,
Pen,
Pgl,
Pyr,
Tic,
Tyr(OMe),
Tyr(OEt), and
Trp(For);
$R^1$ is absent or is $$-NH-(CH_2)_m-\overset{O}{\underset{\|}{C}}-$$

wherein m is an integer of 1, 2, 3, 4, 5, 6, 7, 8, 9, or 10;
$R^2$ is absent or is one to three amino acids selected from the group consisting of:
Ala,
Arg,
Asn,
Asp,
Cys,
Glu,
Gln,
Gly,
His,
Ile,
Leu,
Lys,
Met,
Phe,
Pro,
Ser,
Thr,
Trp,
Tyr,
Val,
HomoPhe,
1-Nal,
2-Nal,
Pgl,
Pyr,
Tic,
Tyr(OMe),
Tyr(OEt), and
Trp(For) and
provided that at least one amino acid is selected from the group consisting of:
His,
Phe,
Trp,
Tyr,
HomoPhe,
1-Nal,
2-Nal,
Pgl,
Pyr,
Tic,
Tyr(OMe),
Tyr(OEt), and
Trp(For);
$AA^{1a}$ is $$-NH-\underset{\underset{R^3}{\overset{\mid}{(CH_2)_n}}}{\overset{\mid}{CH}}-\overset{O}{\underset{\|}{C}}-$$

wherein $R^3$ and n are as defined above;
$AA^2$ is absent or is $$-NH-\underset{\underset{R^5}{\overset{\mid}{(CH_2)_n}}}{\overset{\mid}{CH}}-\overset{O}{\underset{\|}{C}}-$$

wherein $R^5$ is aryl or heteroaryl, and n is as defined above;
$AA^3$ is absent or is $$-NH-\underset{\underset{R^6}{\overset{\mid}{(CH_2)_n}}}{\overset{\mid}{CH}}-\overset{O}{\underset{\|}{C}}-$$

wherein $R^6$ is
hydrogen,
alkyl,
alkenyl,
alkynyl,
cycloalkyl,
heterocycloalkyl,
—$OR^7$, wherein $R^7$ is defined hereinafter,
—$CO_2$—$R^7$ wherein $R^7$ is defined hereinafter, $$-CON-R^7 \atop \phantom{-CON-}\underset{R^{7'}}{\mid}$$

wherein $R^7$ and $R^{7'}$ are each the same or different and each is
hydrogen,
alkyl,
cycloalkyl, or heterocycloalkyl, and
n is as defined above;
AA⁴ is absent or is

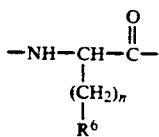

wherein R⁶ and n are as defined above;
AA⁵ is

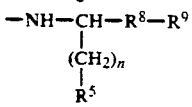

wherein R⁸ is absent or is
alkyl,
alkenyl,
alkynyl,
cycloalkyl, or
heterocycloalkyl,
R⁹ is —CO₂H, or —CH₂OH and
R⁵ and n are as defined above,

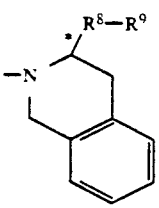

wherein R⁸ and R⁹ are as defined above,

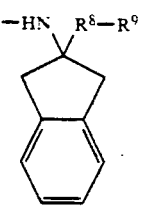

wherein R⁸ and R⁹ are as defined above,

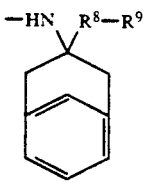

wherein R⁸ and R⁹ are as defined above,

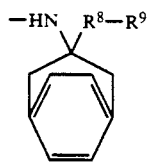

wherein R⁸ and R⁹ are as defined above,

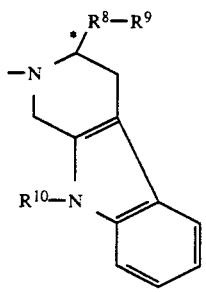

wherein
R¹⁰ is
hydrogen,
alkyl,
formyl, or
acetyl,
R⁸ and R⁹ are as defined above, or

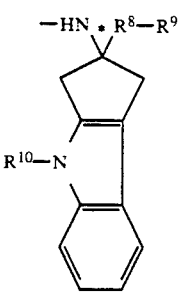

wherein R⁸, R⁹, and R¹⁰ are as defined above, and stereochemistry at CH or C in AA⁵ is L; and with the exclusion of the compound of formula Cys—Ser—Aoc—Val—Tyr—Phe—Cys—His—Leu—Asp—Ile—
Ile—Trp;  Seq. ID NO: 2 or a pharmaceutically acceptable salt thereof.

Elevated levels of endothelin have been postulated to be involved in a number of pathophysiological states including diseases associated with the cardiovascular system as well as various matabolic, neurological, and endocrinological disorders. As antagonists of endothelin, the compounds of Formula I are useful in the treatment of hypertension, myocardial infarction, metabolic, endocrinological and neurological disorders, congestive heart failure, endotoxic shock, subarachnoid hemorrhage, arrhythmias, asthma, acute renal failure, preeclampsia, and diabetes.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, and the like.

The term "alkenyl" means a straight or branched unsaturated hydrocarbon radical having from 2 to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched triple bonded unsaturated hydrocarbon radical having from 2 to 12 carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, 2-undecynyl, 3-undecynyl, 3-dodecynyl, and the like.

The term "cycloalkyl" means a saturated hydrocarbon ring which contains from 3 to 12 carbon atoms, for example, cyclopropyl, cyclobutyl, cyclopentyl, cyclohexyl, adamantyl, and the like.

The terms "alkoxy" and "thioalkoxy" are O-alkyl or S-alkyl as defined above for alkyl.

The term "aryl" means an aromatic radical which is a phenyl group, a benzyl group, a naphthyl group, a pyrenyl group, an anthracenyl group, or a fluorenyl group, unsubstituted or substituted by 1 to 4 substituents selected from alkyl as defined above, alkoxy as defined above, thioalkoxy as defined above, hydroxy, thiol, nitro, halogen, amino,

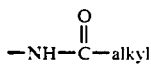

wherein alkyl is as defined above,

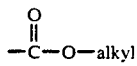

wherein
alkyl is as defined above,

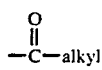

wherein alkyl is as defined above, or aryl.

The term "heteroaryl" means a heteroaromatic radical which is 2- or 3-thienyl, 2- or 3-furanyl, 2-or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3- , 4-, or 5-isoxazolyl, 3- or 5-1,2,4-triazolyl, 4- or 5-1,2,3 triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3- , 4- , 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4- , 5-, 6- , or 7-benzothiazolyl, unsubstituted or substituted by 1 to 2 substituents selected from alkyl as defined above, aryl as defined above, alkoxy as defined above, thioalkoxy as defined above, hydroxy, thiol, nitro, halogen, formyl, amino,

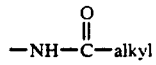

wherein alkyl is as defined above,

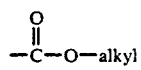

wherein alkyl is as defined above,

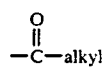

wherein alkyl is as defined above or phenyl.

The term "heterocycloalkyl" means 2- or 3-tetrahydrothieno, 2-or 3-tetrahydrofurano, 2-or 3-pyrrolidino, 2-, 4-, or 5-thiazolidino, 2-, 4-, or 5-oxazolidino, 2- , 3-, or 4-piperidino, N-morpholinyl or N-thiamorpholinyl.

"Halogen" is fluorine, chlorine, bromine or iodine.

The following table provides a list of abbreviations and definitions thereof used in the present invention.

TABLE

| Abbreviation* | |
|---|---|
| | Amino Acid |
| Ala | Alanine |
| Arg | Arginine |
| Asn | Asparagine |
| Asp | Aspartic acid |
| Cys | Cysteine |
| Glu | Glutamic acid |
| Gln | Glutamine |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |
| | Modified and Unusual Amino Acid |
| 3Hyp | 3-Hydroxyproline |
| 4Hyp | 4-Hydroxyproline |
| Hcy | Homocysteine |
| Nva | Norvaline |
| Nle | Norleucine |
| Orn | Ornithine |
| Abu | 4-Aminobutyric acid |
| Ahe | 7-Aminoheptanoic acid |
| Acp | 6-Aminocaproic acid |
| Aoc | 8-Aminooctanoic acid |
| Apn | 5-Aminopentanoic acid |
| Chx | Cyclohexylalanine (Hexahydrophenylalanine) |
| Cit | Citrulline |
| HomoPhe | 2-Amino-5-phenylpentanoic acid (Homophenylalanine) |
| 1-Nal | 3-(1'-Naphthyl)alanine |
| 2-Nal | 3-(2'-Naphthyl)alanine |
| Pen | Penicillamine |
| Pgl | Phenylglycine |
| Pyr | 2-amino-3-(3-pyridyl)-propanoic acid |

TABLE-continued

| Abbreviation* | |
|---|---|
| | (3-Pyridylalanine) |
| Tic | 1,2,3,4-Tetrahydro-3-isoquinolinecarboxylic acid |
| Tyr(OMe) | O-Methyl-tyrosine |
| Tyr(OEt) | O-Ethyl-tyrosine |
| Trp(For) | $N^{in}$-Formyltryptophan |
| Mercapto Acids | |
| Maa | Mercaptoacetic acid |
| Mba | 4-Mercaptobutyric acid |
| Mpa | 3-Mercaptopropionic acid |
| Protecting Group | |
| Ac | Acetyl |
| Ada | 1-Adamantyl acetic acid |
| Adoc | Adamantyloxycarbonyl |
| Bzl | Benzyl |
| MeBzl | 4-Methylbenzyl |
| Z | Benzyloxycarbonyl |
| 2-Br—Z | ortho-Bromobenzyloxycarbonyl |
| 2-Cl—Z | ortho-Chlorobenzyloxycarbonyl |
| Bom | Benzyloxymethyl |
| Boc | tertiary Butyloxycarbonyl |
| Dnp | 2,4-Dinitrophenyl |
| For | Formyl |
| Fmoc | 9-Fluorenylmethyloxycarbonyl |
| $NO_2$ | Nitro |
| Tos | 4-Toluenesulfonyl (tosyl) |
| Trt | Triphenylmethyl (trityl) |
| Solvents and Reagents | |
| HOAc | Acetic acid |
| $CH_3CN$ | Acetonitrile |
| DCM | Dichloromethane |
| DCC | N,N'-Dicyclohexylcarbodiimide |
| DIEA | N,N-Diisopropylethylamine |
| DMF | N,N'-Dimethylformamide |
| HCl | Hydrochloric acid |
| HF | Hydrofluoric acid |
| HOBt | 1-Hydroxybenzotriazole |
| KOH | Potassium hydroxide |
| TFA | Trifluoroacetic acid |
| MBHA Resin | Methylbenzhydrylamine resin |
| PAM Resin | 4-(Oxymethyl)-phenylacetamidomethyl resin |

*If the optical activity of the amino acid is other than L(S), the amino acid or abbreviation is preceded by the appropriate configuration D(R) or DL(RS).

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydroiodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, Berge, S. M., et al, "Pharmaceutical Salts," *Journal of Pharmaceutical Science*, 66, pp. 1-19 (1977)).

The acid addition salts of said basic compounds are prepared by contacting the free base form with a sufficient amount of the desired acid to produce the salt in the conventional manner. Preferably a peptide of Formula I can be converted to an acidic salt by treating with an aqueous solution of the desired base, such that the resulting pH is less than 4. The solution can be passed through a C18 cartridge to absorb the peptide, washed with copious amounts of water, the peptide eluted with a polar organic solvent such as, for example, methanol, acetonitrile, and the like, and isolated by concentrating under reduced pressure followed by lyophilization. The free base form may be regenerated by contacting the salt form with a base and isolating the free base in the conventional manner or as above. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts," *Journal of Pharmaceutical Science*, 66, pp. 1-19 (1977)).

The base addition salts of said acidic compounds are prepared by contacting the free acid form with a sufficient amount of the desired base to produce the salt in the conventional manner. Preferably, a peptide of Formula I can be converted to a base salt by treating with an aqueous solution of the desired base, such that the resulting pH is greater than 9. The solution can be passed through a C18 cartridge to absorb the peptide, washed with copious amounts of water, the peptide eluted with a polar organic solvent such as, for example, methanol, acetonitrile and the like, and isolated by concentrating under reduced pressure followed by lyophilization. The free acid form may be regenerated by contacting the salt form with an acid and isolating the free acid in the conventional manner or as above. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of Formula I is one wherein $AA^1$ is

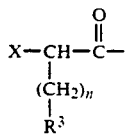

wherein
X is
  hydrogen,
  alkyl, or
  cycloalkyl,
n is zero or an integer of 1, 2, 3, 4, 5, or 6,
$R^3$ is —S—$R^4$ wherein $R^4$ is as defined hereinafter,

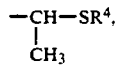

wherein $R^4$ is as defined hereinafter,
—C(CH$_3$)$_2$—S—$R^4$, wherein $R^4$ is
  hydrogen,
  alkyl or $R^4$ is absent when $AA^1$ is covalently linked to $AA^{1a}$ through a disulfide bridge,

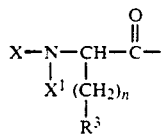

wherein X and $X^1$ are each the same or different and each is as defined above for X or $X^1$ is Asp-Lys-Glu and $R^3$ and n are as defined above or

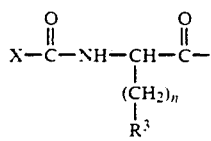

wherein X, n, and $R^3$ are as defined above;
R is absent or is one to four amino acids selected from the group consisting of:
Ala,
Asn,
Asp,
Gln,
Glu,
Ile,
Leu,
Lys,
3Hyp,
4Hyp,
Nle,
Orn,
Ser,
Thr, and
Val;
$AA^{1a}$ is selected from the group consisting of:
Cys,
Hcy, and
Pen
  which may or may not be covalently linked to $AA^1$ through a disulfide bridge;

$AA^2$ is absent or is selected from the group consisting of:
His,
Phe,
Tyr,
Trp,
Trp(For),
Tyr(OMe),
Tyr(OEt),
Pyr,
2-Nal, and
1-Nal;
$AA^3$ is absent or is selected from the group consisting of:
Ala,
Asn,
Gln,
Gly,
Ile,
Leu,
Met,
Val,
Nva,
Nle,
Chx, and
Abu;
$AA^4$ is absent or is selected from the group consisting of:
Asn,
Asp,
Gln,
Glu, and
Cit;
$AA^5$ is selected from the group consisting of:
Trp,
Tyr,
Trp(For),
2-Nal, and
1-Nal A more preferred compound of Formula I is one wherein
$AA^1$ is selected from the group consisting of:
Asp-Lys-Glu-Cys,
Cys,
Hcy,
Pen,
Maa,
Mba, and
Mpa;
R is $R^a$—$R^b$—$R^c$—$R^b$ wherein
$R^a$ is absent or is selected from the group consisting of:
3Hyp,
4Hyp,
Ser, and
Thr,
$R^b$ is absent or is selected from the group consisting of:
Asn,
Asp,
Gln, and
Glu,
$R^c$ is absent or is selected from the group consisting of:
Ile,
Leu,
Lys,
Nle, Orn, and
Val.
Particularly valuable are:

Cys—Val—Tyr—Phe—Cys—His—Leu—Asp—Ile—Ile—Trp;     Seq. ID NO: 3

Cys—Ser—Ahe—Val—Phe—Cys—His—Leu—Asp—Ile—Ile—Trp;     Seq. ID NO: 4

Cys—Ser—Val—Tyr—Phe—Cys—His—Leu—Asp—Ile—Ile—Trp;     Seq. ID NO: 5

Cys—Ser—Ser—Val—Tyr—Phe—Cys—His—Leu—Asp—Ile—Ile—Trp;     Seq. ID NO: 6

Cys—Ser—Ser—Ser—Val—Tyr—Cys—His—Leu—Asp—Ile—Ile—Trp;     Seq. ID NO: 7

Cys—Ser—Ser—Ser—Tyr—Phe—Cys—His—Leu—Asp—Ile—Ile—Trp;     Seq. ID NO: 8

Cys—Ser—Ahe—Val—Tyr—D—Phe—Cys—His—Leu—Asp—Ile—Ile—Trp;

Cys—Ser—Ahe—Val—Tyr—Phe—Cys—Phe—Leu—Asp—Ile—Ile—Trp;     Seq. ID NO: 9

Cys—Ser—Acp—Val—Tyr—Phe—Cys—His—Leu—Asp—Ile—Ile—Trp;     Seq. ID NO: 10

Cys—Ser—Ahe—Val—Tyr—Phe—Cys—His—Leu—Asp—Ile—Ile—Trp;     Seq. ID NO: 11

Cys—Ser—Ahe—Val—Tyr—Phe—Cys—D—Phe—Leu—Asp—Ile—Ile—Trp;

Cys—Ser—Apn—Val—Tyr—Phe—Cys—His—Leu—Asp—Ile—Ile—Trp;     Seq. ID NO: 12

Cys—Thr—Ahe—Val—Tyr—Phe—Cys—His—Leu—Asp—Ile—Ile—Trp;     Seq. ID NO: 13

Cys—Ser—Ser—Ser—Val—Tyr—Phe—Cys—His—Leu—Asp—Ile—Ile—Trp;     Seq. ID NO: 14

Cys—Ser—Ser—Ser—Tyr—Phe—Phe—Cys—D—His—Leu—Asp—Ile—Ile—Trp;

Cys—Ser—Ser—Ser—Val—Tyr—Phe—Cys—His—Leu—Asp—Ile—D—Ile—Trp;

Cys—Ser—Ser—Ser—Val—Tyr—Phe—Cys—D—Phe—Leu—Asp—Ile—Ile—Trp;

Cys—Ser—Asp—Lys—Glu—Val—Tyr—Phe—Cys—His—Leu—Asp—Ile—Ile—Trp;     Seq. ID NO: 15

Cys—Ser—Asp—Leu—Glu—Val—Tyr—Phe—Cys—His—Leu—Asp—Ile—Ile—Trp;     Seq. ID NO: 16

Cys—Ser—Asn—Lys—Gln—Val—Tyr—Phe—Cys—His—Leu—Asp—Ile—Ile—Trp; and     Seq. ID NO: 17

Asp—Lys—Glu—Cys—Val—Tyr—Phe—Cys—His—Leu—Asp—Ile—Ile—Trp;     Seq. ID NO: 18

-continued
or a pharmaceutically acceptable acid or base addition salt thereof.

The compounds of Formula I are valuable antagonists of endothelin. The test employed indicate that compounds of Formula I possess endothelin antagonist activity. Thus, the compounds of Formula I were tested for their ability to inhibit [$^{125}$I]-ET-1([$^{125}$I]-Endothelin-1) binding in a receptor assay. The binding of the compounds of Formula I is determined by incubation (37° C., 2 hours) of a compound of Formula I with [$^{125}$I]-ET-1 and the tissue (rat heart ventricle (10 μg)) in 50 mM Tris(hydroxymethyl)aminomethane hydrochloride (Tris-HCl) (pH 7.4), 5 mM ethylenediamine tetraacetic acid (EDTA), 2 mM ethylene glycol bis(β-aminoethyl ether)N,N,N',N'-tetraacetic acid (EGTA), 100 μM phenylmethylsulfonyl fluoride (PMSF), and 100 μM bacitracin containing protease inhibitors (total volume of 0.5 mL). IC$_{50}$ values are calculated by weighing nonlinear regression curve-fitting to the mass-action (Langmuir) equation. The functional activity of compounds of Formula I is determined in Rat-1 cells by measuring intracellular levels of second messengers. Thus, cells are prelabeled with [$^3$H]-inositol and endothelin-stimulated accumulation of total [$^3$H]-inositol phosphates in the presence of Li$^+$ is monitored using anion exchange chromatography as described by Muldoon, L. L., et al, *Journal of Biological Chemistry*, Volume 264, pages 8529–8536 (1989) and Dudley, D. T., et al, *Molecular Pharmacology*, Volume 38, pages 370–377 (1990). Antagonist activity is assessed as the ability of added compounds to reduce endothelin stimulated inositol phosphate accumulation. The data in the table show the endothelin antagonist activity of representative compounds of Formula I.

TABLE 1

| | Biological Activity of Compounds of Formula I | | |
|---|---|---|---|
| Example Number | Compound | Binding Assay in Rat Heart Ventricle IC$_{50}$ (μM) or % Inhibition | IP (Inositol Phosphate) Accumulation. (Rat Skin Fibroblasts) IC$_{50}$ (μM) |
| 1 | Cys—Val—Tyr—Phe—Cys—His—Leu—Asp—Ile—Ile—Trp; Seq ID NO: 3 | 6.5 | 2.2 |
| 2 | Cys—Ser—Ser—Ser—Val—Tyr—Phe—Cys—His—Leu—Asp—Ile—Ile—Trp Seq ID NO: 14 | 2.07/1.17* | 5.0 |
| 3 | Cys—Ser—Ahe—Val—Tyr—Phe—Cys—His—Leu—Asp—Ile—Ile—Trp Seq ID NO: 11 | 2.5 | 8.0 |
| 4 | Cys—Ser—Ahe—Val—Tyr—D—Phe—Cys—His—Leu—Asp—Ile—Ile—Trp Seq ID NO: 12 | 0.66 | 9.2 |
| 5 | Cys—Ser—Apn—Val—Tyr—Phe—Cys—His—Leu—Asp—Ile—Ile—Trp Seq ID NO: 10 | 1.8 | 30 |
| 6 | Cys—Ser—Acp—Val—Tyr—Phe—Cys—His—Leu—Asp—Ile—Ile—Trp | 100% inhibition @ 10$^{-5}$ | |
| 7 | Cys—Ser—Asp—Lys—Glu—Val—Tyr—Phe—Cys—His—Leu—Asp—Ile—Ile—Trp Seq ID NO: 15 | 3.5 | |
| 8 | Cys—Ser—Ser—Val—Tyr—Phe—Cys—His—Leu—Asp—Ile—Ile—Trp Seq ID NO: 6 | 1.82 | |
| 9 | Cys—Ser—Val—Tyr—Phe—Cys—His—Leu—Asp—Ile—Ile—Trp Seq ID NO: 5 | 2.83 | |
| 10 | Cys—Ser—Asp—Leu—Glu—Val—Tyr—Phe—Cys—His—Leu—Asp—Ile—Ile—Tyr Seq ID NO: 16 | 3.2 | |
| 11 | Asp—Lys—Glu—Cys—Val—Tyr—Phe—Cys—His—Leu—Asp—Ile—Ile—Trp Seq ID NO: 18 | 0.94 | |

TABLE 1-continued

Biological Activity of Compounds of Formula I

| Example Number | Compound | Binding Assay in Rat Heart Ventricle IC$_{50}$ (μM) or % Inhibition | IP (Inositol Phosphate) Accumulation. (Rat Skin Fibroblasts) IC$_{50}$ (μM) |
|---|---|---|---|
| 12 | Cys—Ser—Asn—Lys—Gln—Val—Tyr—Phe—Cys—His—Leu—Asp—Ile—Ile—Trp  Seq ID NO: 17 (Cys-Cys cyclized) | >10 μM | |
| 13 | Cys—Ser—Ser—Ser—Val—Tyr—Phe—Cys—D-Phe—Leu—Asp—Ile—Ile—Trp (Cys-Cys cyclized) | 4.8 | 16.1 |
| 14 | Cys—Ser—Ser—Ser—Val—Tyr—Phe—Cys—His—Leu—Asp—Ile—D—Ile—Trp (Cys-Cys cyclized) | 2.6 | 0.75 |

*Two independent test results

General Method for Preparing Compounds of Formula I

The compounds of Formula I may be prepared by solid phase peptide synthesis on a peptide synthesizer, for example, an Applied Biosystems 430A peptide synthesizer using activated esters or anhydrides of N-alpha-Boc protected amino acids, on PAM or MBHA resins. Additionally, the compounds of Formula I may also be prepared by conventional solution peptide synthesis. Amino acid side chains are protected as follows: Bzl(Asp, Glu, Ser), 2-Cl-Z(Lys), 2-Br-Z(Tyr), Bom(His), For(Trp), and MeBzl(Cys). Each peptide resin (1.0 g) is cleaved with 9 mL of HF and 1 mL of anisole or p-cresol as a scavenger (60 minutes, 0° C.). The peptide resin is washed with cyclohexane, extracted with 30% aqueous HOAc, followed by glacial HOAc, concentrated under reduced pressure, and lyophilized. (A peptide containing For(Trp) is dissolved in 0° C., the pH is adjusted to 12.5 with 1N KOH (2 minutes), neutralized with glacial HOAc, desalted on C$_{18}$ and lyophilized.) The peptide is dissolved in water (~0.2 mg/mL) at pH 8–9 (adjusted and maintained with dilute ammonium hydroxide) and dithiothreitol (~100 mg) is added. After 1 hour, the peptide solution is titrated with dilute aqueous potassium ferricyanide (~0.01 N) until a yellow solution is obtained and maintained for 2 hours. The pH is adjusted to <4.0 with acetic acid and a weak anion exchange resin is added (50 equivalents). After 1 hour, the resin is filtered and the solution passed through a C$_{18}$ cartridge, washed with water and the peptide eluted with acetonitrile with 10–30% H$_2$O and 0.1% TFA. The solution is concentrated under reduced pressure and lyophilized. The crude cyclic peptide is purified by preparative reversed phase high performance liquid chromatography (RP-HPLC) on a C$_{18}$ column (2.2×25.0 cm, 15.0 mL/min) with a linear gradient of 0.1% TFA in water to 0.1% TFA in acetonitrile and lyophilized. The homogeneity and composition of the resulting peptide is verified by RP-HPLC, capillary electrophoresis, thin layer chromatography (TLC), proton nuclear magnetic resonance spectrometry (NMR), and fast atom bombardment mass spectrometry (FAB-MS).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonist of endothelin, the compounds utilized in the pharmaceutical methods of this invention are administered at the initial dosage of about 0.01 mg to about 20 mg per kilogram daily. A daily dose range of about 0.01 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred methods for preparing the compounds of the invention.

EXAMPLE 1

Seq ID NO: 3

```
┌─────────────────────────┐
Cys—Val—Tyr—Phe—Cys—His—Leu—Asp—Ile—Ile—Trp
```

The title compound is prepared by standard solid phase synthetic peptide methodology utilizing a Boc/-benzyl strategy (Stewart, J. M. and Young, J. D., *Solid Phase Peptide Synthesis*, Pierce Chemical Co., Rockford, Ill., 1984). All protected amino acids and reagents are obtained from commercial sources and are not further purified. The protected peptide resin is prepared on an Applied Biosystems 430A Peptide Synthesizer, utilizing protocols supplied for a dicyclohexylcarbodiimide mediated coupling scheme (Standard 1.0, Version 1.40). Starting with 0.69 meq of N-α-Boc-Trp(For)-PAM resin (0.72 meq/g, 0.50 meq of Boc-Trp(For) total) the protected peptide is prepared by the stepwise coupling of the following amino acids (in order of addition): Boc-Cys(4MeBzl); Boc-Val; Boc-Tyr(2-Br-Z); Boc-Phe; Boc-Cys(4Me-Bzl); Boc-His(Dnp); Boc-Leu $H_2O$; Boc-Asp(OBzl); Boc-Ile 0.5 $H_2O$; and Boc-Ile 0.5 $H_2O$. A typical cycle for the coupling of an individual amino acid residue is illustrated below (reproduced from the ABI manual):

All the single couple RV cycles conform to the following pattern:
1) 33% TFA in DCM for 80 seconds
2) 50% TFA in DCM for 18.5 minutes
3) Three DCM washes
4) 10% DIEA in DMF for 1 minute
5) 10% DIEA in DMF for 1 minute
6) Five DMF washes
7) Coupling period
8) five DCM washes After coupling the last amino acid the protected resin is treated with 10% thiophenol in DMF (1×60 min), DMF (2×1 min), DCM (2×1 min), 50% TFA in DCM (2×10 min), DCM (3×1 min), 10% DIEA in DMF (2×2 min), 10% piperidine in DMF (1×120 min, 0° C.), DCM (3×1 min), and dried under reduced pressure (1.32 g).

The peptide is liberated from the solid support, and the carboxylate of aspartic acid deprotected by treatment with anhydrous hydrogen fluoride (9.0 mL), anisole (0.5 mL), and dimethyl sulfide (0.5 mL) (60 minutes, 0° C.). After removing the hydrogen fluoride under a stream of nitrogen, the resin is washed with cyclohexane (3×20 mL) and extracted with glacial HOAc (3×30 mL) and TFA (1×20 mL). The aqueous extractions are combined, concentrated under reduced pressure, diluted with $H_2O$, and lyophilized (350 mg). The peptide is dissolved in water (3.5 L) and the pH is adjusted to 11 to clarify the solution (1N KOH), readjusted to 7.5 with 10% aqueous HOAc and dithiothreitol (200 mg) is added. After 1 hour, the peptide solution is titrated with dilute aqueous potassium ferricyanide (~0.01 N) until a yellow solution is obtained and maintained for 1 hour. The pH is adjusted to <4.0 with acetic acid and a weak anion exchange resin is added (50 equivalents). After 1 hour, the resin is filtered and the solution passed through a C18 cartridge, washed with water, and the peptide eluted with 30% aqueous acetonitrile with 0.1% TFA (100 mL). The solution is concentrated under reduced pressure and lyophilized. The crude peptide is dissolved in 4.0 mL of 50% TFA/$H_2O$, filtered through a 0.4 μM syringe filter, and chromatographed on a Vydac 218TP 1022 column (2.2×25.0 cm, 15.0 mL/min, A: 0.1% TFA/$H_2O$, B: 0.1% TFA/$CH_3CN$, Gradient; 0% B for 10 minutes, 10% to 50% B over 120 minutes). Individual fractions are collected and combined based upon analysis by analytical HPLC. The combined fractions are concentrated under reduced pressure (10 mL), diluted with $H_2O$ (50 mL), and lyophilized (62.0 mg). The homogeneity and structure of the resulting peptide is confirmed by analytical HPLC, capillary zone electrophoresis, Proton Nuclear Magnetic Resonance Spectroscopy (H¹-NMR) and Fast Atom Bombardment Mass Spectroscopy (FAB-MAS), MH+ 1410.3.

In a process analogous to Example 1 using the appropriate amino acids, the corresponding compounds of Formula I are prepared as follows:

EXAMPLE 2

Cys—Ser—Ser—Ser—Val—Tyr—Phe—Cys—His—Leu—Asp—Ile—Ile—Trp:
FAB-MS. MH⁻ 1670.6.

EXAMPLE 3

Cys—Ser—Ahe—Val—Tyr—Phe—Cys—His—Leu—Asp—Ile—Ile—Trp:
FAB-MS. MH⁺ 1625.0.

EXAMPLE 4

Cys—Ser—Ahe—Val—Tyr—D—Phe—Cys—His—Leu—Asp—Ile—Ile—Trp:
FAB-MS. MH⁺ 1625.0

EXAMPLE 5

Seq. ID NO: 12

Cys—Ser—Apn—Val—Tyr—Phe—Cys—His—Leu—Asp—Ile—Ile—Trp:
FAB-MS. MH⁺ 1610.3.

EXAMPLE 6

Seq. ID NO: 10

Cys—Ser—Acp—Val—Tyr—Phe—Cys—His—Leu—Asp—Ile—Ile—Trp;
FAB-MS, MH⁺ 1624.1.

EXAMPLE 7

Seq. ID NO: 15

Cys—Ser—Asp—Lys—Glu—Val—Tyr—Phe—Cys—His—Leu—Asp—Ile—Ile—Trp:
FAB-MS, MH⁺ 1869.9.

EXAMPLE 8

Seq ID. NO: 6

Cys—Ser—Ser—Val—Tyr—Phe—Cys—His—Leu—Asp—Ile—Ile—Trp:
FAB-MS. MH⁺ 1583.6.

EXAMPLE 9

Seq. ID NO: 14

Cys—Ser—Val—Tyr—Phe—Cys—His—Leu—Asp—Ile—Ile—Trp:
FAB-MS. MH⁺ 1497.4.

EXAMPLE 10

Seq. ID NO: 11

Cys—Ser—Asp—Leu—Glu—Val—Tyr—Phe—Cys—His—Leu—Asp—Ile—Ile—Trp:
FAB-MS. MH⁺ 1855.7.

EXAMPLE 11

Seq. ID NO: 16

Seq. ID NO: 18

Asp—Lys—Glu—Cys—Val—Tyr—Phe—Cys—His—Leu—Asp—Ile—Ile—Trp:
FAB-MS. MH⁻ 1781.7.

EXAMPLE 12

```
  ┌─────────────────────────────────────────┐
  Cys—Ser—Asn—Lys—Gln—Val—Tyr—Phe—Cys—His—Leu—Asp—Ile—Ile—Trp;
FAB-MS, MH⁺ 1868.5.
```

EXAMPLE 13

Seq. ID NO: 17

```
                          ┌─────────────────────────────────────────┐
  Cys—Ser—Ser—Ser—Val—Tyr—Phe—Cys—D—Phe—Leu—Asp—Ile—Ile—Trp;
FAB-MS, MH⁺ 1681.3.
```

EXAMPLE 14

```
                          ┌─────────────────────────────────────────┐
  Cys—Ser—Ser—Ser—Val—Tyr—Phe—Cys—His—Leu—Asp—Ile—D—Ile—Trp;
FAB-MS, MH⁺ 1672.9.
```

---

We claim:

1. A compound of formula I $$AA^1-R-R^1-R^2-AA^{1a}-AA^2-AA^3-AA^4-AA^3-AA^3-AA^5 \quad \text{I}$$

wherein
$AA_1$ is

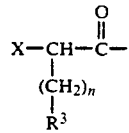

wherein
X is
    hydrogen,
    alkyl,
    alkenyl,
    alkynyl,
    cycloalkyl,
    heterocycloalkyl,
    aryl, or
    heteroaryl,
n is zero or an integer of 1 or 2,
$R^3$ is $-S-R^4$, wherein $R^4$ is as defined hereinafter,

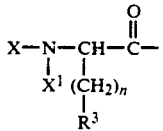

wherein $R^4$ is as defined hereinafter,
$-C(CH_3)_2-S-R^4$, wherein $R^4$ is covalently linked to $AA^{1a}$ through a disulfide bridge,

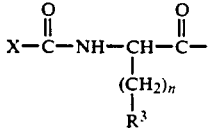

wherein X is as defined above, $X^1$ is hydrogen or Asp-Lys-Glu and n and $R^3$ are as defined above, $$X-\overset{O}{\underset{}{C}}-NH-CH-\overset{O}{\underset{}{C}}-$$
$$\qquad\qquad\qquad |$$
$$\qquad\qquad\quad (CH_2)_n$$
$$\qquad\qquad\qquad |$$
$$\qquad\qquad\qquad R^3$$

wherein X, n, and $R^3$ are as defined above, or

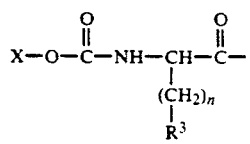

wherein X, n, and $R^3$ are as defined above;
R is absent or is one to four amino acids selected from the group consisting of:
Asn,
Asp,
Glu,
Gln,
Lys,
Ser,
Thr,
Val, and
Orn,
$R^1$ is absent or is

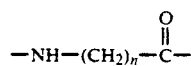

wherein m is an integer of 1, 2, 3, 4, 5, 6, 7, 8, 9, or 10;
$R^2$ is absent or is one to three amino acids selected from the group consisting of:
Ala,
Ile,
Leu,
Phe,
Trp,
Tyr,
Val,
HomoPhe,
1-Nal,
2-Nal,
Pgl,
Pyr,
Tic
Tyr(OMe),
Tyr(OEt), and
Trp(FOR) and
provided that at least one amino acid is selected from the group consisting of:
Phe,
Trp,
Tyr,
HomoPhe,
1-Nal,
2-Nal,
Pgl,
Pyr,
Tic,
Tyr(OMe),
Tyr(OEt), and
Trp(For);
$AA^{1a}$ is

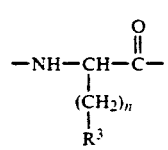

wherein $R^3$ and n are as defined above;

$AA^2$ is

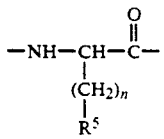

wherein
$R^5$ is phenyl, 4-hydroxy phenyl, 4-alkoxy phenyl, or naphthyl or, 3-indolyl unsubstituted or substituted by formyl on the indole nitrogen, and
n is as defined above;
$AA^3$ is

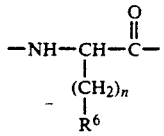

wherein
$R^6$ is
hydrogen,
alkyl,
alkenyl,
alkynyl,
cycloalkyl,
heterocycloalkyl,
—$OR^7$, wherein $R^7$ is defined hereinafter,
—$CO_2$—$R^7$ wherein $R^7$ is defined hereinafter,

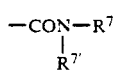

wherein $R^7$ and $R^{7'}$ are each the same or different and each is
hydrogen,
alkyl,
cycloalkyl, or
heterocycloalkyl, and
n is as defined above;
$AA^4$ is

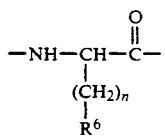

wherein $R^6$ and n are as defined above;
$AA^5$ is

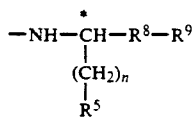

wherein
$R^8$ is
alkyl,
alkenyl,
alkynyl,
cycloalkyl, or
heterocycloalkyl, $R^9$ is $-CO_2H$, or $-CH_2OH$ and
$R^5$ and n are as defined above,
stereochemistry at CH or C in $AA^5$ is L; and with the exclusion of the compound of the formula

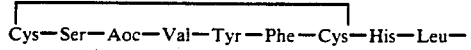

or a pharmaceutically acceptable salt thereof.

2. A compound according to claim 1, in which $AA^1$ is

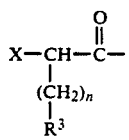

wherein
X is
  hydrogen,
  alkyl, or
  cycloalkyl,
n is zero or an integer of 1, or 2
$R^3$ is $-S-R^4$ wherein $R^4$ is as defined hereinafter,

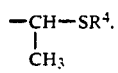

wherein $R^4$ is as defined hereinafter,
$-C(CH_3)_2-S-R^4$, wherein $R^4$ is covalently linked to $AA^{1a}$ through a disulfide bridge,

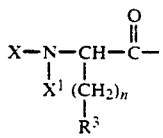

wherein X is as defined above $X^1$ is hydrogen or Asp-Lys-Glu and $R^3$ and n are as defined above or

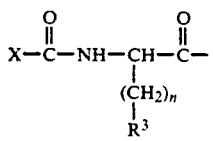

wherein X, n and $R^3$ are as defined above;
R is absent or is one to four amino acids selected from the group consisting of:
Asn,
Asp,
Gln,
Glu,
Lys,
Orn,
Ser,
Thr, and
Val;

$AA^{1a}$ is selected from the group consisting of:
Cys,
Hcy, and
Pen
which is covalently linked to $AA^1$ through a disulfide bridge;
$AA^2$ is selected from the group consisting of:
Phe,
Tyr,
Trp,
Trp(For),
Tyr(OMe),
Tyr(OEt),
2-Nal, and
1-Nal;
$AA^3$ is selected from the group consisting of:
Ala,
Asn,
Gln,
Gly,
Ile,
Leu,
Met,
Val,
Nva,
Nle,
CHx, and
Abu;
$AA^4$ is selected from the group consisting of:
Asn,
Asp,
Gln,
Glu, and
Cit;
$AA^5$ is selected from the group consisting of:
Trp,
Tyr,
Trp(For),
2-Nal, and
1-Nal.

3. A compound according to claim 2, in which $AA^1$ is selected from the group consisting of:
Asp-Lys-Glu-Cys,
Cys,
Hcy,
Pen,
Maa,
Mba, and
Mpa;
R is $R^a-R^b-R^c-R^b$ wherein
  $R^a$ is absent or is selected from the group consisting of:
    Ser, and
    Thr,
  $R^b$ is absent or is selected from the group consisting of:
    Asn,
    Asp,
    Gln, and
    Glu,
  $R^c$ is absent or is selected from the group consisting of:
    Lys,
    Orn, and
    Val.

4. A compound according to claim 3 selected from the group consisting of:

Cys—Val—Tyr—Phe—Cys—His—Leu—Asp—Ile—Ile—Trp;    Seq. ID NO: 3

Cys—Ser—Ahe—Val—Phe—Cys—His—Leu—Asp—Ile—Ile—Trp;    Seq. ID NO: 4

Cys—Ser—Val—Tyr—Phe—Cys—His—Leu—Asp—Ile—Ile—Trp;    Seq. ID NO: 5

Cys—Ser—Ser—Val—Tyr—Phe—Cys—His—Leu—Asp—Ile—Ile—Trp;    Seq. ID NO: 6

Cys—Ser—Ser—Ser—Val—Tyr—Cys—His—Leu—Asp—Ile—Ile—Trp;    Seq. ID NO: 7

Cys—Ser—Ser—Ser—Tyr—Phe—Cys—His—Leu—Asp—Ile—Ile—Trp;    Seq. ID NO: 8

Cys—Ser—Ahe—Val—Tyr—D—Phe—Cys—His—Leu—Asp—Ile—Ile—Trp;

Cys—Ser—Ahe—Val—Tyr—Phe—Cys—Phe—Leu—Asp—Ile—Ile—Trp;    Seq. ID NO: 9

Cys—Ser—Acp—Val—Tyr—Phe—Cys—His—Leu—Asp—Ile—Ile—Trp;    Seq. ID NO: 10

Cys—Ser—Ahe—Val—Tyr—Phe—Cys—His—Leu—Asp—Ile—Ile—Trp;    Seq. ID NO: 11

Cys—Ser—Ahe—Val—Tyr—Phe—Cys—D—Phe—Leu—Asp—Ile—Ile—Trp;

Cys—Ser—Apn—Val—Tyr—Phe—Cys—His—Leu—Asp—Ile—Ile—Trp;    Seq. ID NO: 12

Cys—Thr—Ahe—Val—Tyr—Phe—Cys—His—Leu—Asp—Ile—Ile—Trp;    Seq. ID NO: 13

Cys—Ser—Ser—Ser—Val—Tyr—Phe—Cys—His—Leu—Asp—Ile—Ile—Trp;    Seq. ID NO: 14

Cys—Ser—Ser—Ser—Tyr—Phe—Phe—Cys—D—His—Leu—Asp—Ile—Ile—Trp;

Cys—Ser—Ser—Ser—Val—Tyr—Phe—Cys—His—Leu—Asp—Ile—D—Ile—Trp;

Cys—Ser—Ser—Ser—Val—Tyr—Phe—Cys—D—Phe—Leu—Asp—Ile—Ile—Trp;

Cys—Ser—Asp—Lys—Glu—Val—Tyr—Phe—Cys—His—Leu—Asp—Ile—Ile—Trp;    Seq. ID NO: 15

Cys—Ser—Asp—Leu—Glu—Val—Tyr—Phe—Cys—His—Leu—Asp—Ile—Ile—Trp;    Seq. ID NO: 16

Cys—Ser—Asn—Lys—Gln—Val—Tyr—Phe—Cys—His—Leu—Asp—Ile—Ile—Trp; and    Seq. ID NO: 17

Asp—Lys—Glu—Cys—Val—Tyr—Phe—Cys—His—Leu—Asp—Ile—Ile—Trp.    Seq. ID NO: 18

5. A method of inhibiting elevated levels of endothelin comprising administering to a host suffering therefrom a therapeutically effective amount of a compound according to claim 1 in unit dosage form.

6. A pharmaceutical composition adapted for administration as an antagonist of endothelin; as an antihypertensive agent; as an agent for treating metabolic and endocrine disorders; as an agent for treating congestive heart failure and myocardial infarction; as an agent for treating endotoxic shock; a an agent for treating subarachnoid hemorrhage; as an agent for treating arrhythmias; as an agent for treating asthma; as an agent for treating acute renal failure; as an agent for treating preeclampsia; as an agent for treating diabetes; and as an agent for treating neurologic disorders comprising a therapeutically effective amount of a compound according to claim 1 in admixture with a pharmaceutically acceptable excipient, diluent, or carrier.

7. A method of treating hypertension comprising administering to a host suffering therefrom a therapeutically effective amount of a compound according to claim 1 in unit dosage form.

* * * * *

UNITED STATES PATENT AND TRADEMARK OFFICE
CERTIFICATE OF CORRECTION

PATENT NO. : 5,260,276
DATED : Nov. 9, 1993
INVENTOR(S) : Cody, et al

It is certified that error appears in the above-indentified patent and that said Letters Patent is hereby corrected as shown below:

Column 33, line 44, delete "(FOR)" and insert instead "(For)".

Column 35, line 2, at the end of the line, insert the word "and".

Column 35, line 3, delete "CH" and insert instead "CH*".

Column 35, line 3, delete "C" and insert instead "C*".

Signed and Sealed this

Sixth Day of September, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,260,276
DATED : November 9, 1993
INVENTOR(S) : Cody, et al

It is certified that error appears in the above-indentified patent and that said Letters Patent is hereby corrected as shown below:

Column 31, line 42, at the end of the line insert
-- Seq. ID NO: 1 --.

Column 31, line 45, the subscript "1" should be a superscript "1".

Column 35, line 10, at the end of the line insert
-- Seq. ID NO: 2 --.

Signed and Sealed this

Twentieth Day of December, 1994

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Xaa  Xaa  Xaa  Xaa  Xaa  Xaa  Xaa  Xaa  Xaa  Xaa  Xaa
1                  5                        10
```

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i x ) FEATURE:
        ( A ) NAME/KEY: Disulfide-bond
        ( B ) LOCATION: 1..7

( x i ) SEQUENCE DESCRIPTION: SEQ ID NO:2:

```
Cys  Ser  Xaa  Val  Tyr  Phe  Cys  His  Leu  Asp  Ile  Ile  Trp
1                  5                        10
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Disulfide-bond
        ( B ) LOCATION: 1..5

( x i ) SEQUENCE DESCRIPTION: SEQ ID NO:3:

```
Cys  Val  Tyr  Phe  Cys  His  Leu  Asp  Ile  Ile  Trp
```

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..6

(xi) SEQUENCE DESCRIPTION: SEQ ID NO:4:

Cys Ser Xaa Val Phe Cys His Leu Asp Ile Ile Trp
    1              5                        10

(2) INFORMATION FOR SEQ ID NO:5:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..6

(xi) SEQUENCE DESCRIPTION: SEQ ID NO:5:

Cys Ser Val Tyr Phe Cys His Leu Asp Ile Ile Trp
    1              5                        10

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..7

(xi) SEQUENCE DESCRIPTION: SEQ ID NO:6:

Cys Ser Ser Val Tyr Phe Cys His Leu Asp Ile Ile Trp
    1              5                        10

(2) INFORMATION FOR SEQ ID NO:7:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..7

(xi) SEQUENCE DESCRIPTION: SEQ ID NO:7:

Cys Ser Ser Ser Val Tyr Cys His Leu Asp Ile Ile Trp
    1                5                  10

(2) INFORMATION FOR SEQ ID NO:8:

(i) SEQUENCE CHARACTERISTICS:

(A) LENGTH: 13 amino acids
(B) TYPE: amino acid
(D) TOPOLOGY: linear ( i i ) MOLECULE TYPE: peptide ( i x ) FEATURE:
(A) NAME/KEY: Disulfide-bond
(B) LOCATION: 1..7

( x i ) SEQUENCE DESCRIPTION: SEQ ID NO:8:

Cys Ser Ser Ser Tyr Phe Cys His Leu Asp Ile Ile Trp
1               5                   10

( 2 ) INFORMATION FOR SEQ ID NO:9:

( i ) SEQUENCE CHARACTERISTICS:
(A) LENGTH: 13 amino acids
(B) TYPE: amino acid
(D) TOPOLOGY: linear ( i i ) MOLECULE TYPE: peptide ( i x ) FEATURE:
(A) NAME/KEY: Disulfide-bond
(B) LOCATION: 1..7

( x i ) SEQUENCE DESCRIPTION: SEQ ID NO:9:

Cys Ser Xaa Val Tyr Phe Cys Phe Leu Asp Ile Ile Trp
1               5                   10

( 2 ) INFORMATION FOR SEQ ID NO:10:

( i ) SEQUENCE CHARACTERISTICS:
(A) LENGTH: 13 amino acids
(B) TYPE: amino acid
(D) TOPOLOGY: linear ( i i ) MOLECULE TYPE: peptide ( i x ) FEATURE:
(A) NAME/KEY: Disulfide-bond
(B) LOCATION: 1..7

( x i ) SEQUENCE DESCRIPTION: SEQ ID NO:10:

Cys Ser Xaa Val Tyr Phe Cys His Leu Asp Ile Ile Trp
1               5                   10

( 2 ) INFORMATION FOR SEQ ID NO:11:

( i ) SEQUENCE CHARACTERISTICS:
(A) LENGTH: 13 amino acids
(B) TYPE: amino acid
(D) TOPOLOGY: linear ( i i ) MOLECULE TYPE: peptide ( i x ) FEATURE:
(A) NAME/KEY: Disulfide-bond
(B) LOCATION: 1..7

( x i ) SEQUENCE DESCRIPTION: SEQ ID NO:11:

Cys Ser Xaa Val Tyr Phe Cys His Leu Asp Ile Ile Trp
1               5                   10

( 2 ) INFORMATION FOR SEQ ID NO:12:

( i ) SEQUENCE CHARACTERISTICS:
(A) LENGTH: 13 amino acids
(B) TYPE: amino acid
(D) TOPOLOGY: linear ( i i ) MOLECULE TYPE: peptide (ix) FEATURE:
    (A) NAME/KEY: Disulfide-bond
    (B) LOCATION: 1..7

(xi) SEQUENCE DESCRIPTION: SEQ ID NO:12:

Cys Ser Xaa Val Tyr Phe Cys His Leu Asp Ile Ile Trp
1                     5                             10

(2) INFORMATION FOR SEQ ID NO:13:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..7

(xi) SEQUENCE DESCRIPTION: SEQ ID NO:13:

Cys Thr Xaa Val Tyr Phe Cys His Leu Asp Ile Ile Trp
1                     5                             10

(2) INFORMATION FOR SEQ ID NO:14:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..8

(xi) SEQUENCE DESCRIPTION: SEQ ID NO:14:

Cys Ser Ser Ser Val Tyr Phe Cys His Leu Asp Ile Ile Trp
1                     5                             10

(2) INFORMATION FOR SEQ ID NO:15:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..9

(xi) SEQUENCE DESCRIPTION: SEQ ID NO:15:

Cys Ser Asp Lys Glu Val Tyr Phe Cys His Leu Asp Ile Ile Trp
1                     5                             10                   15

(2) INFORMATION FOR SEQ ID NO:16:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..9

(xi) SEQUENCE DESCRIPTION: SEQ ID NO:16:

```
Cys  Ser  Asp  Leu  Glu  Val  Tyr  Phe  Cys  His  Leu  Asp  Ile  Ile  Trp
 1              5                        10                            15
```

(2) INFORMATION FOR SEQ ID NO:17:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..9

(xi) SEQUENCE DESCRIPTION: SEQ ID NO:17:

```
Cys  Ser  Asn  Lys  Gln  Val  Tyr  Phe  Cys  His  Leu  Asp  Ile  Ile  Trp
 1              5                        10                            15
```

(2) INFORMATION FOR SEQ ID NO:18:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 4..8

(xi) SEQUENCE DESCRIPTION: SEQ ID NO:18:

```
Asp  Lys  Glu  Cys  Val  Tyr  Phe  Cys  His  Leu  Asp  Ile  Ile  Trp
 1              5                        10
```